US00PP29307P3

(12) United States Plant Patent
Suphachadiwong

(10) Patent No.: US PP29,307 P3
(45) Date of Patent: May 22, 2018

(54) ***VANDA* PLANT NAMED 'SPCDW1514'**

(50) Latin Name: ***Vanda* Jones ex R. Br..**
Varietal Denomination: SPCDW1514

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 22 days.

(21) Appl. No.: 15/330,351

(22) Filed: Sep. 9, 2016

(65) Prior Publication Data

US 2017/0196148 P1 Jul. 6, 2017

(30) Foreign Application Priority Data

Sep. 15, 2015 (QZ) ..... PBR 2015/2163

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Anne Marie Grunberg
(74) *Attorney, Agent, or Firm* — Samuel R. McCoy, Jr.

(57) ABSTRACT

A new and distinct *Vanda* plant named 'SPCDW1514' which is characterized by sepals and petals which are yellow and fading to green-yellow at the margins and apex, sepals and petals which are moderately to heavily dotted greyed-purple, a labellum with yellow-green lateral lobes and a dark yellow-green central lobe which is dotted and blotched greyed-purple, as well as the stability of these characteristics from generation to generation.

4 Drawing Sheets

Latin name of the genus and species: The Latin name of the genus and species of the novel variety disclosed herein is *Vanda* Jones ex R. Br..

Variety denomination: The inventive variety of *Vanda* disclosed herein has been given the variety denomination 'SPCDW1514'.

CROSS REFERENCE TO RELATED APPLICATIONS

This application claims priority to the Community Plant Variety Rights application number 2015/2163, filed Sep. 15, 2015, which is herein incorporated by reference.

BACKGROUND OF THE INVENTION

Parentage: The *Vanda* variety 'SPCDW1514' is the result of a planned breeding program. The new variety originated as a seedling from the crossing of an unnamed *Vanda* seed parent (not patented) with an unnamed *Vanda* pollen parent (not patented). Both parents were developed by, and are owned by, the inventor and were never commercially released. The crossing was made by the inventor in his research greenhouse in Bangphra, Thailand in November of 1994.

The new variety was first selected in December of 1999, in a research greenhouse in Bangphra, Thailand belonging to the inventor. After identifying the new variety as a potentially interesting selection, the inventor continued confidential testing and propagation of 'SPCDW1514', assessing stability of the unique characteristics of this variety.

Asexual Reproduction: Asexual reproduction of the new cultivar 'SPCDW1514', by way of mericloning, was first initiated in December of 2009 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1514' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1514'. These characteristics in combination distinguish 'SPCDW1514' as a new and distinct *Vanda* cultivar:

1. *Vanda* 'SPCDW1514' exhibits sepals and petals which are yellow and fading to green-yellow at the margins and apex; and
2. *Vanda* 'SPCDW1514' exhibits sepals and petals which are moderately to heavily dotted greyed-purple; and
3. *Vanda* 'SPCDW1514' exhibits a labellum with yellow-green lateral lobes, and a dark yellow-green central lobe which is dotted and blotched greyed-purple.

BOTANICAL DESCRIPTION OF THE PLANT

Figure 1:
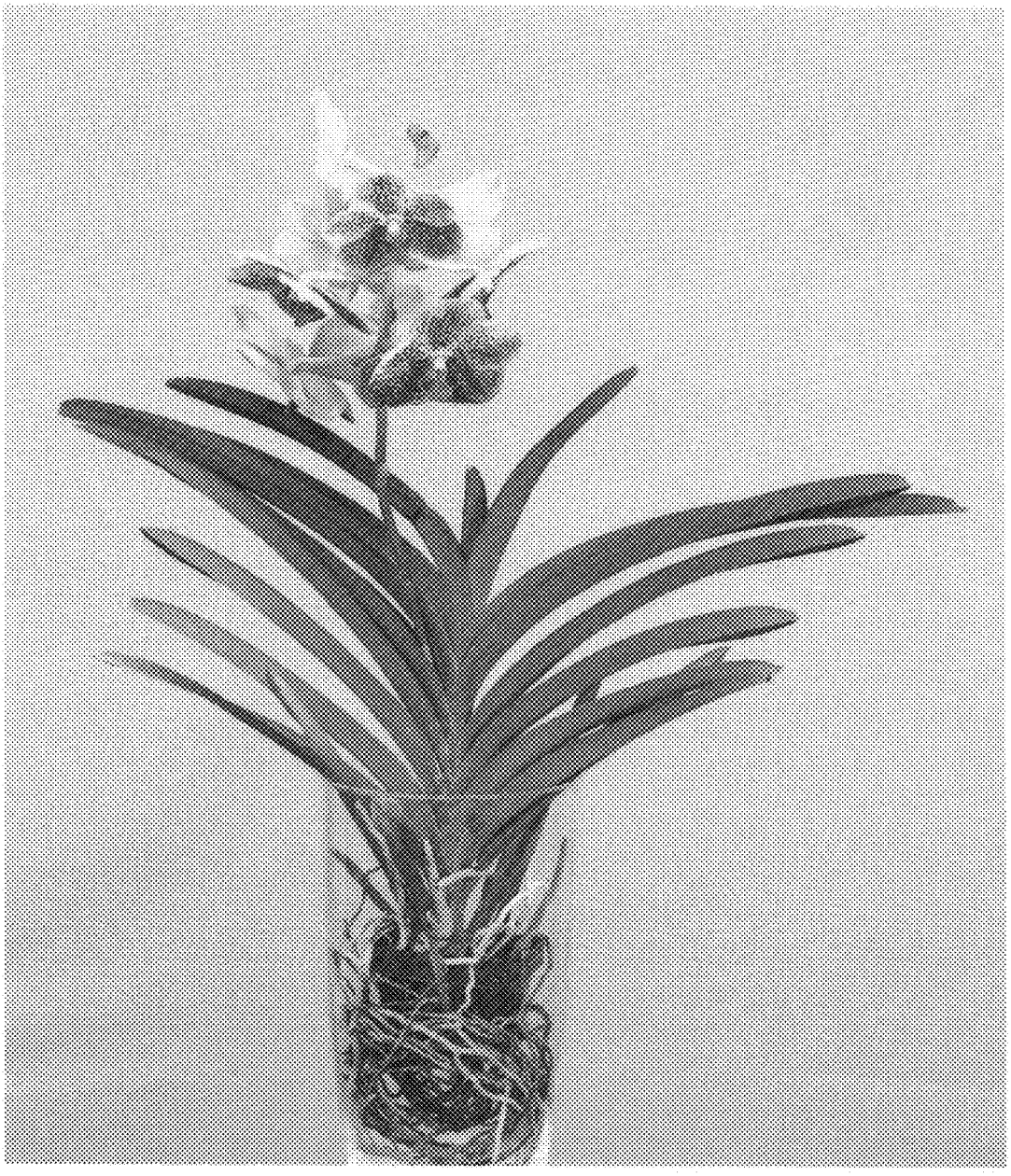
FIG. 1 illustrates, as nearly true as it is reasonably possible to make the same in color photographs of this type, an exemplary plant of 'SPCDW1514' grown in a commercial greenhouse in Honselersdijk, the Netherlands. This plant is approximately 6 years old from the time of mericloning, shown planted in an 8 by 8 cm container.
Figure 2:
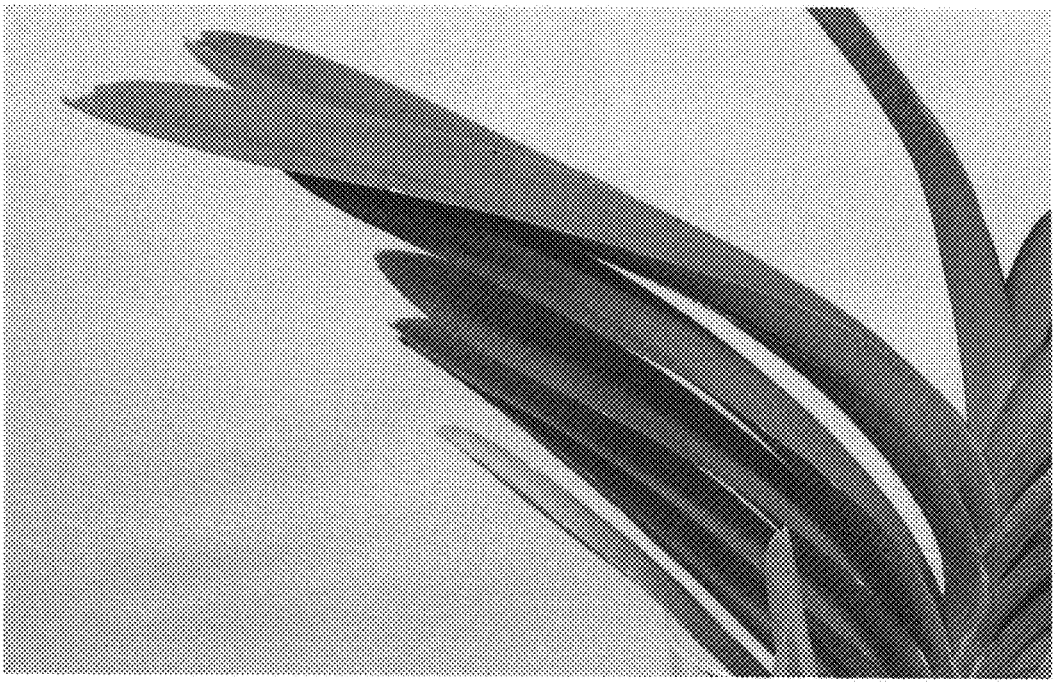
FIG. 2 illustrates, as nearly true as it is reasonably possible to make the same in color photographs of this type, the typical foliage of 'SPCDW1514'.
Figure 3:
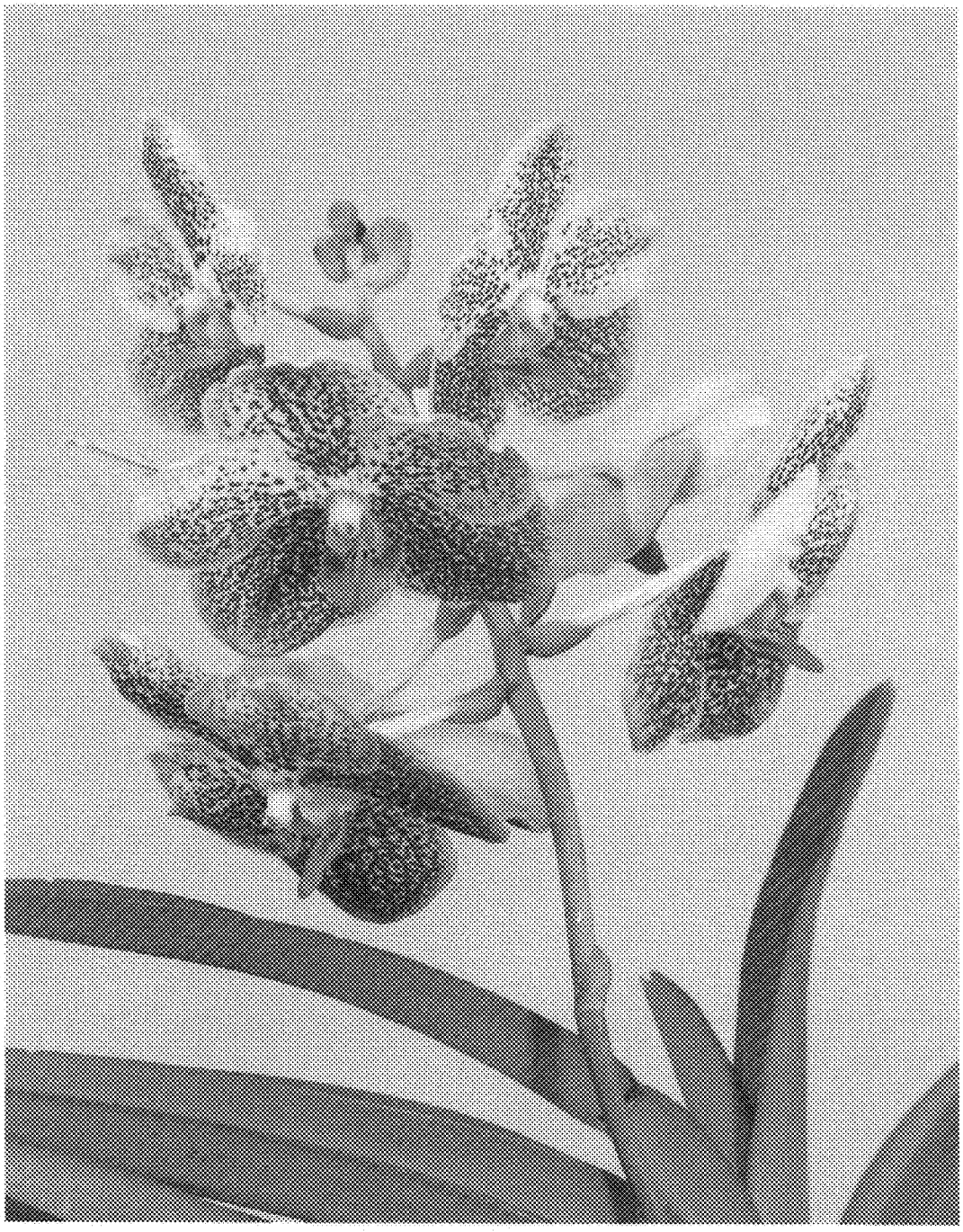
FIG. 3 illustrates, as nearly true as it is reasonably possible to make the same in color photographs of this type, the typical inflorescence of 'SPCDW1514'.
Figure 4:
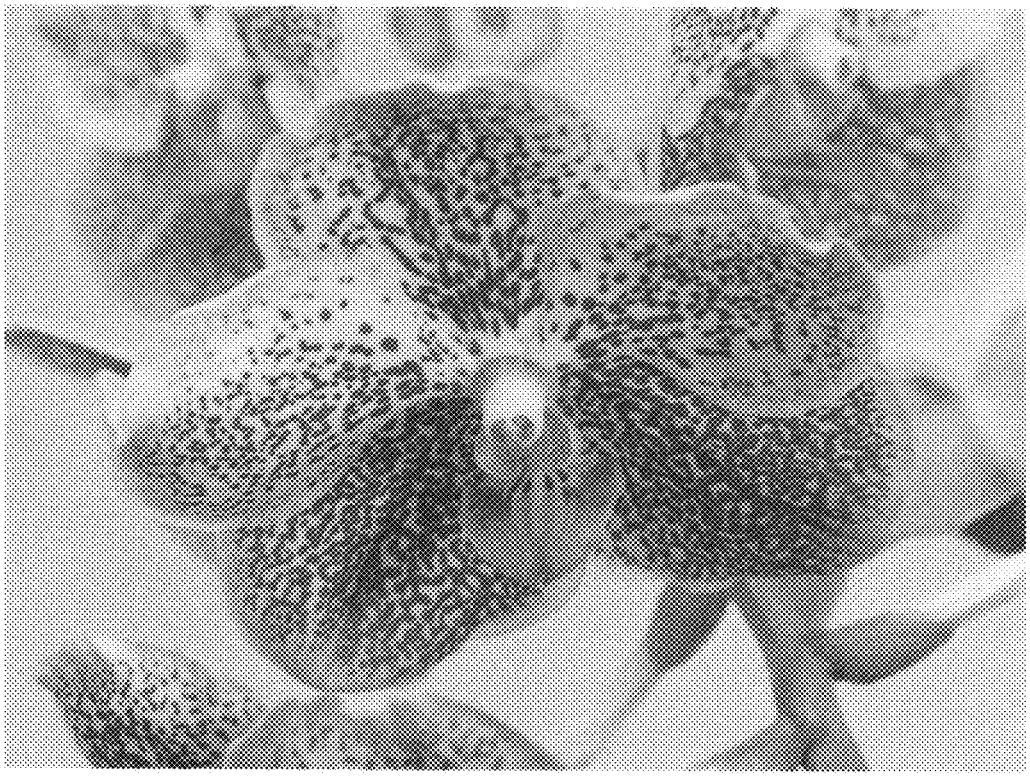
FIG. 4 illustrates, as nearly true as it is reasonably possible to make the same in color photographs of this type, the typical flower of 'SPCDW1514'.

The following observations and measurements made in August of 2016 describe averages from a sample set of six specimens of six year-old 'SPCDW1514' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1514' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1514' and comparisons with other varieties of *Vanda* are provided below.

Plant description:

- *Growth habit.*—Perennial; monopodial, upright. Single monopodial leafy stem, with flowers carried slightly above the leaf plane with inflorescences growing from the leaf axils.
- *Average height from base (plant grown in hanging basket, so no soil line present) to foliar plane.*—36.0 cm.
- *Average height from base (plant grown in hanging basket, so no soil line present) to top of floral plane.*—49.9 cm.
- *Plant spread.*—Average of 50.1 cm.
- *Appropriate container size.*—8 cm by 8 cm rectangular hanging basket.
- *Growth rate.*—Moderate.
- *Plant vigor.*—Moderate.
- *Propagation type.*—Tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Similar to other *Vanda* varieties.
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Densely rooting; with aerial roots only.
- *Dimensions, mature roots.*—57.1 cm long with a diameter of 0.35 cm, on average.
- *Texture.*—Very fleshy; non-fibrous.
- *Color.*—Greyed-Green, near RHS 192B; root apex is yellow-green, RHS 146B.

Stem:

- *Branching habit.*—Monopodial; no lateral branches present.
- *Number of primary (main) stems per plant.*—One.
- *Number of secondary (lateral) branches per plant.*—None.
- *Appearance and shape.*—Circular, formed by the leaf sheaths.
- *Length.*—19.9 cm.
- *Diameter.*—0.9 cm.
- *Internode length.*—0.8 cm.
- *Luster.*—Matte.
- *Aspect.*—Near vertical.
- *Strength.*—Very strong.
- *Color, juvenile.*—Yellow-green, near RHS 145D.
- *Color, mature.*—Yellow-green, near RHS 145D.
- *Color at internodes.*—Yellow-green, near RHS 145D.
- *Pubescence.*—Glabrous.

Foliage:

- *Arrangement.*—Distichous.
- *Dimensions.*—25.6 cm long and 1.9 cm wide, on average.
- *Shape of blade.*—Ligulate; strongly carinate.
- *Aspect.*—Moderately curved.
- *Apex.*—Unequal praemorse.
- *Base.*—Sheathing.
- *Sheath dimensions.*—3.3 cm long and 1.3 cm wide, on average.
- *Sheath color.*—Yellow-green, near RHS 150B.
- *Margin.*—Entire.
- *Pubescence, texture and luster of adaxial surface.*—Glabrous, smooth, and very slightly glossy.
- *Pubescence, texture and luster of abaxial surface.*—Glabrous, smooth, and matte.
- *Color.*—Juvenile foliage, adaxial surface — Green, near RHS 143C; much darker at the margins, RHS 137A to 137B. Juvenile foliage, abaxial surface — Yellow-green, near RHS 144A. Mature foliage, adaxial surface — Green, near RHS 143A. Mature foliage, abaxial surface — Yellow-green, near RHS 146C.
- *Venation.*—Parallel.
- *Venation color, adaxial surface.*—Green, near RHS 143A.
- *Venation color, abaxial surface.*—Yellow-green, near RHS 146C.
- *Petiole.*—No petioles present; leaves sessile.

Inflorescence:

- *Inflorescence arrangement.*—Axially placed raceme.
- *Natural flowering season.*—Autumn into winter.
- *Time to flower.*—Approximately 10 months.
- *Flowers per inflorescence.*—Average of 12; 9 open flowers and 3 buds.

*Inflorescence height.*—Approximately 18.0 cm (measured from base of lowest flower to top of upper flower).

*Inflorescence diameter.*—Approximately 16.0 cm.

*Peduncle.*—Dimensions — Approximately 30.5 cm long and 0.5 cm wide. Aspect — Generally at a 25 degree angle to lateral branch axis. Strength — Moderately strong. Texture and luster — Glabrous and moderately glossy. Color — Green, near RHS 143B to 143C.

Bud:

*Length.*—Average of 1.3 cm.

*Diameter.*—Average horizontal diameter is 1.1 cm; the vertical diameter is 1.4 cm.

*Shape.*—Cubic, with a small deltoid apex which is pointed downward.

*Pubescence, texture and luster.*—Glabrous, smooth and matte.

*Color.*—Yellow-green, near RHS 150D; apex is darker, near RHS 154D.

Flower:

*Flower type.*—Zygomorphic (orchidaceous), typical shape for the genus *Vanda*.

*Flowering habit.*—Moderate.

*Shape.*—Zygomorphic, single; consisting of three sepals and three petals, one of which is transformed into a labellum.

*Aspect.*—Flowers are outward-facing to slightly nodding.

*Vertical height.*—Approximately 8.8 cm.

*Diameter.*—Approximately 8.6 cm.

*Depth.*—Approximately 3.1 cm.

*Fragrance.*—No fragrance.

*Lastingness.*—3 weeks, on average.

*Persistent.*—Self-cleaning.

*Petals.*—Quantity of Petals — Three unfused petals; two conventional petals and one labellum. Arrangement — One lateral petal on each side. Length — Approximately 4.3 cm. Width — Approximately 4.0 cm. Shape — Broad ovate. Apex — Obtuse. Base — Cuneate. Margin — Entire; slightly undulated. Pubescence, texture and luster of upper surface — Glabrous, velvety and matte. Pubescence, texture and luster of lower surface — Glabrous, velvety and matte. Color when opening, upper surface — In between green-yellow, near RHS 1C, and yellow, near RHS 3C; moderately to heavily dotted greyed-purple, near RHS 183C. Color when opening, lower surface — Yellow, near RHS 3D. Color when fully opened, upper surface — Yellow, near RHS 3C, and fading to yellow-green towards the margins and apex, near RHS 154B; moderately to heavily dotted greyed-purple, near RHS 183C. Color when fully opened, lower surface — Yellow, near RHS 3D, and fading to green-yellow towards the margins and apex, slightly darker than near RHS 1A. Fading, upper surface — Not fading. Fading, lower surface — Not fading. Venation — Densely reticulate. Venation color, fully opened, upper surface — Yellow, near RHS 3C, and fading to yellow-green towards the margins and apex, near RHS 154B. Venation color, fully opened, lower surface — Yellow, near RHS 3D, and fading to green-yellow towards the margins and apex, slightly darker than near RHS 1A.

*Labellum.*—Shape — Three-lobed, lateral lobes are involute and the central lobe is revolute. Length — Central lobe — Approximately 1.7 cm. Lateral lobes — Approximately 0.7 cm. Width — Control lobe — Approximately 1.7 cm. Lateral lobes — Approximately 0.6 cm. Apex, central lobe — Emarginate. Apex, lateral lobes — Obtuse. Base, central and lateral lobes — Cuneate. Margin, central lobe — Finely and irregularly toothed; not undulate. Margin, lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and very slightly glossy. Lateral lobes — Glabrous, velvety, and matte. Color when opening, upper surface — Central lobe — Yellow-green, near RHS 151A to 151B, and yellow-green, RHS 146C, at the apex; dotted and blotched with greyed-purple, near RHS 184B, at the base. Lateral lobes — Yellow-green, near RHS 150B. Color when opening, lower surface — Central lobe — Yellow-green, near RHS 151A to 151B, and yellow-green, RHS 146C, at the apex; dotted and blotched with greyed-purple, near RHS 184B, at the base. Lateral lobes — Yellow-green, near RHS 150B. Color when fully opened, upper surface — Central lobe — Yellow-green, slightly darker than near RHS N144A; dotted and blotched with greyed-purple, near RHS 184A. Lateral lobes — Yellow-green, in between near RHS 144C and 145A. Color when fully opened, lower surface — Central lobe — Yellow-green, near RHS N144A, and fading lighter towards the base, near RHS 145C; dotted and blotched with greyed-purple, near RHS 184A to 184B. Lateral lobes — Yellow-green, near RHS 145A. Fading, upper surface — Not fading. Fading, lower surface — Not fading. Venation — Densely reticulate. Venation color, fully opened, upper surface — Central lobe — Yellow-green, slightly darker than near RHS N144A; dotted and blotched with greyed-purple, near RHS 184A. Lateral lobes — Yellow-green, in between near RHS 144C and 145A. Venation color, fully opened, lower surface — Central lobe — Yellow-green, near RHS N144A, and fading lighter towards the base, near RHS 145C; dotted and blotched with greyed-purple, near RHS 184A to 184B. Lateral lobes — Yellow-green, near RHS 145A.

*Callosities.*—Dimensions — 1.4 cm long and 0.6 cm wide, on average. Color — Yellow-green, slightly darker than near RHS N144A.

*Spurs.*—Quantity — Average of 1. Length — Approximately 0.9 cm. Diameter — Approximately 0.3 cm. Vertical height — Approximately 0.7 cm, at the base. Shape — Short triangular. Apex — Bluntly acute. Base — Broad Cuneate. Pubescence, texture and luster — Glabrous, smooth, and matte. Color — Yellow-green, near RHS 150B.

*Sepals.*—Quantity — Average of 3 unfused sepals. Arrangement — One dorsal sepal and two lateral sepals. Length — Dorsal sepal — Approximately 4.4 cm. Lateral sepals — Approximately 4.4 cm. Width — Dorsal sepal — Approximately 4.3 cm. Lateral sepals — Approximately 5.1 cm. Shape — Dorsal sepal — Broad ovate. Lateral sepals — Broad deltoid. Apex, dorsal and lateral sepals — Obtuse. Base, dorsal and lateral sepals — Cuneate. Margin, dorsal and lateral sepals — Entire; slightly undulated. Pubescence, texture and luster — Glabrous, velvety, and matte on both the upper and lower sepal surfaces. Color when opening, upper surface — Dorsal sepal — In between green-yellow, near RHS 1C, and yellow, near RHS 3C; moderately to heavily dotted greyed-purple, near RHS 183C. Lateral sepals — In between green-yellow, near RHS 1C, and yellow, near RHS 3C; heavily dotted greyed-purple, near RHS 183C. Color when opening, lower surface — Dorsal sepal — Yellow, near RHS 3D. Lateral sepals — Yellow, near RHS 3D. Color when fully opened, upper surface — Dorsal sepal — Yellow, near RHS 3C, and fading to yellow-green, near RHS 154B, towards the margins and apex; moderately to heavily dotted greyed-purple, near RHS 183C. Lateral sepals — Yellow-green, near RHS 154B, and fading darker, near RHS 151B, towards the margins and apex; heavily dotted greyed-purple, near RHS 183B to 183C. Color when fully opened, lower surface — Dorsal sepal — In between green-yellow, near RHS 1A, to yellow-green, near RHS 151C. Lateral sepals — In between green-yellow, near RHS 1A, to yellow-green, near RHS 151C. Fading, upper surface — Not fading. Fading, lower surface — Not fading. Venation — Densely reticulate. Venation color, fully opened, upper surface — Dorsal sepal — Yellow, near RHS 3C, and fading to yellow-green, near RHS 154B, towards the margins and apex; moderately to heavily dotted greyed-purple, near RHS 183C. Lateral sepals — Yellow-green, near RHS 154B, and fading darker, near RHS 151B, towards the margins and apex; heavily dotted greyed-purple, near RHS 183B to 183C. Venation color, fully opened, lower surface — Dorsal sepal — In between green-yellow, near RHS 1A, to yellow-green, near RHS 151C. Lateral sepals — In between green-yellow, near RHS 1A, to yellow-green, near RHS 151C.

*Pedicels.*—Length — Approximately 5.2 cm. Diameter — Approximately 0.4 cm. Angle — Approximately 95 degree angle to peduncle axis, varying between 90 and 100 degrees. Strength — Moderate. Texture — Glabrous, axially angled with 5 "ribs", axially twisted (due to resupination). Luster — Glossy. Color — Yellow-green, near RHS 145C, and fading darker, near RHS 145A to 145B, towards the proximal end.

*Bract.*—Quantity — One bract present at the base of each pedicel. Shape — Broad ovate; folded around the base of each pedicel. Dimensions — Average of 1.5 cm long and 1.3 cm wide. Apex — Obtuse. Base — Broad cuneate. Margins — Entire. Color, both surfaces — Yellow-green, near RHS 144A to 144B.

Reproductive organs:

*Column.*—Length — Approximately 0.6 cm. Diameter — Approximately 0.6 cm. Color — Yellow-green near RHS 145B to 145C.

*Ovary.*—Position — Inferior Diameter — Approximately 0.3 cm. Color — Yellow-green, RHS 145D.

*Pollinia color.*—Yellow-orange, RHS 13B.

Seed and fruit: No fruit and seed production has been detected to date.

COMPARISON WITH THE PARENT PLANTS

Plants of the new cultivar 'SPCDW1514' differ from the unnamed *Vanda* seed parent (not patented) by the characteristics described in Chart 1.

CHART 1

| Characteristic | 'SPCDW1514' | Unnamed seed parent |
|---|---|---|
| Inflorescence. | Racemes are longer with more flowers on each raceme compared to the seed parent. | Racemes are shorter with fewer flowers on each raceme compared to the 'SPCDW1514'. |
| Flower size. | Smaller than the seed parent. | Larger than 'SPCDW1514'. |
| Plant vigor. | More vigorous; easier to cultivate and quicker to flower when compared to the seed parent. | Less vigorous; more difficult to cultivate and slower to flower when compared to 'SPCDW1514'. |

Plants of the new cultivar 'SPCDW1514' differ from the unnamed *Vanda* pollen parent (not patented) by the characteristics described in Chart 2.

CHART 2

| Characteristic | 'SPCDW1514' | Unnamed pollen parent |
|---|---|---|
| Flower color. | Darker yellow. | Lighter yellow. |
| Color pattern on the petals and sepals. | More heavily dotted. | Lightly dotted. |
| Floriferousness. | Free flowering. | Not freely flowering. |
| Lastingness of flowers. | Long lasting. | Not long lasting. |

COMPARISON WITH THE MOST SIMILAR *VANDA* CULTIVAR KNOWN TO THE INVENTOR

Plants of the new cultivar 'SPCDW1514' are most similar to the cultivar, *Vanda* 'SPCDW1406' (U.S. Plant Pat. No. 28,324). A comparison of 'SPCDW1514' with *Vanda* 'SPCDW1406' is described in Chart 3.

CHART 3

| Characteristic | 'SPCDW1514' | 'SPCDW1406' |
|---|---|---|
| Leaf width. | 1.9 cm. | 2.7 cm. |
| Flower, vertical height. | 8.8 cm. | 10.0 cm. |
| Flower, diameter. | 8.6 cm. | 8.5 cm. |
| Petal dimensions. | 4.3 cm long and 4.0 cm wide. | 4.4 cm long and 4.4 cm wide. |
| Petal color; upper surface, when opening. | In between green-yellow, near RHS 1C, and yellow, near RHS 3C; moderately to heavily dotted greyed-purple, near RHS 183C. | Yellow, near RHS 4D, and darker towards the margins and tip, near RHS 3D to 4C; tinged greyed-yellow towards the tip, near RHS 161D; dotted red-purple at the base, near RHS 59A. |
| Petal color; lower surface, when opening | Yellow, near RHS 3D. | Yellow, in between near RHS 4C and 4D, and tinged greyed-yellow towards the tip and margins, near RHS 161D. |

CHART 3-continued

| Characteristic | 'SPCDW1514' | 'SPCDW1406' |
|---|---|---|
| Petal color; upper surface, when fully open. | Yellow, near RHS 3C, and fading to yellow-green towards the margins and apex, near RHS 154B; moderately to heavily dotted greyed-purple, near RHS 183C. | Yellow, near RHS 5D, and slightly darker towards the margins, RHS 6D; tinged greyed-yellow towards the tip, near RHS 161D; dotted greyed-purple at the base, near RHS 183A. |
| Petal color; lower surface, when fully open. | Yellow, near RHS 3D, and fading to yellow-green towards the margins and apex, slightly darker than near RHS 1A. | Yellow, near RHS 6D, and tinged greyed-yellow towards the tip and margins, near RHS 162C. |
| Labellum color; upper surface when fully open. | Lateral lobes are yellow-green, in between near RHS 144C and 145A. Central lobe is yellow-green, slightly darker than near RHS N144A; dotted and blotched greyed-purple, near RHA 184A. | Lateral lobes are yellow-green, near RHS 154B, and finely dotted greyed-purple at the base, near RHS 183B. Central lobe is greyed-orange, near RHS 175A, and fading to yellow-green at the base, near RHS 154D. |
| Labellum color; lower surface when fully open. | Lateral lobes are yellow-green, near RHS 145A. Central lobe is yellow-green, near RHS N144A, and fading lighter towards the base, near RHS 145C; dotted and blotched greyed-purple, near RHS 184A to 184B. | Lateral lobes are yellow-green, near RHS 154C. Central lobe is yellow-green, near RHS 154C to 154D; margins and apex are greyed-orange, near RHS 177B, and finely dotted greyed-purple at the base, near RHS 183D. |
| Dorsal sepal length. | 4.4 cm. | 4.9 cm. |
| Lateral sepal length. | 4.4 cm. | 5.2 cm. |
| Sepal color; upper surface, when fully open. | Dorsal sepal is yellow, near RHS 3C, and fading to yellow-green towards the margins and apex, near RHS 154B; moderately to heavily dotted greyed-purple, near RHS 183C. Lateral sepals are yellow-green, near RHS 154B, and fading darker towards the margins and apex, near RHS 151B; heavily dotted greyed-purple, near RHS 183B to 183C. | Dorsal sepal is yellow, near RHS 5D, and slightly darker towards the margins, RHS 6D; tinged greyed-yellow towards the tip, near RHS 161D; dotted greyed-purple at the base, near RHS 183A. |
| Sepal color; lower surface, when fully open. | Dorsal sepal and lateral sepals are in between green-yellow, near RHS 1A, and yellow-green, near RHS 151C. | Dorsal sepal is yellow, near RHS 3C to 3D, and tinged greyed-yellow towards the apex and margins, near RHS 161B; heavily dotted greyed-purple, near RHS 183A. Lateral sepals are green-yellow to yellow, near RHS 1C to 5D, and tinged greyed-yellow towards the margins and apex, near RHS 162A to 162B. |
| Spur dimensions. | 0.9 cm long, 0.3 cm in diameter, and 0.7 cm in vertical height. | 0.7 cm long, 0.3 cm in diameter, and 0.6 cm in vertical height. |
| Spur color. | Yellow-green, near RHS 150B. | Yellow, near RHS 4C. |

That which is claimed is:

1. A new and distinct variety of *Vanda* plant named 'SPCDW1514', substantially as described and illustrated herein.

* * * * *